United States Patent [19]

Phillips

[11] Patent Number: 5,037,444

[45] Date of Patent: Aug. 6, 1991

[54] PROSTHETIC FOOT

[76] Inventor: Van L. Phillips, 4702 San Jacinto Ter., Fallbrook, Calif. 92028

[21] Appl. No.: 293,824

[22] Filed: Jan. 5, 1989

[51] Int. Cl.$^5$ ............................................. A61F 2/66
[52] U.S. Cl. ....................................... 623/55; 623/53
[58] Field of Search ................................. 623/53–55, 623/56

[56] References Cited

U.S. PATENT DOCUMENTS

| | | | |
|---|---|---|---|
| 2,075,583 | 3/1937 | Lange | 3/8 |
| 3,335,428 | 8/1967 | Gajdos | 3/7 |
| 3,754,286 | 8/1973 | Ryan | 623/55 |
| 3,833,941 | 9/1974 | Wagner | 3/7 |
| 3,874,004 | 4/1975 | May | 3/7 X |
| 3,890,650 | 6/1975 | Prahl | 3/7 |
| 4,091,472 | 5/1978 | Daher et al. | 3/7 |
| 4,177,525 | 12/1979 | Arbogast et al. | 3/7 |
| 4,180,872 | 1/1980 | Chaikin | 3/7 |
| 4,225,982 | 10/1980 | Cochrane et al. | 3/7 |
| 4,302,856 | 12/1981 | May | 3/7 X |
| 4,306,320 | 12/1981 | Delp | 3/7 |
| 4,328,594 | 5/1982 | Campbell et al. | 3/7 |
| 4,360,931 | 11/1982 | Hampton | 3/7 X |
| 4,547,913 | 10/1985 | Phillips | 623/27 |
| 4,636,220 | 1/1987 | Ziegelmeyer | 623/53 |
| 4,645,509 | 2/1987 | Poggi et al. | 623/55 |
| 4,721,510 | 1/1988 | Cooper et al. | 623/55 |
| 4,822,363 | 4/1989 | Phillips | 623/53 |
| 4,892,553 | 1/1990 | Prahl | 623/55 |
| 4,959,073 | 9/1990 | Merlette | 623/55 |

FOREIGN PATENT DOCUMENTS

| | | | |
|---|---|---|---|
| 2626463 | 8/1989 | France | 623/53 |
| 8800815 | 2/1988 | World Int. Prop. O. | 623/53 |
| 8909036 | 10/1989 | World Int. Prop. O. | 623/53 |

Primary Examiner—Randall L. Green
Assistant Examiner—David H. Willse
Attorney, Agent, or Firm—J. Mark Holland; Thomas P. Mahoney

[57] ABSTRACT

A prosthetic foot characterized by a forefoot portion having a heel portion demountably and interchangeably connected thereto. The forefoot portion and heel portion are fabricated from polymer impregnated and encapsulated laminates, including such laminates as carbon fibers and/or fiberglas or synthetic fibers such as Kevlar. The demountable connection of the heel portion permits interchangeability of heel and forefoot portions to match the weight, stride and activity schedule of the wearer utilizing the prosthetic foot.

23 Claims, 3 Drawing Sheets

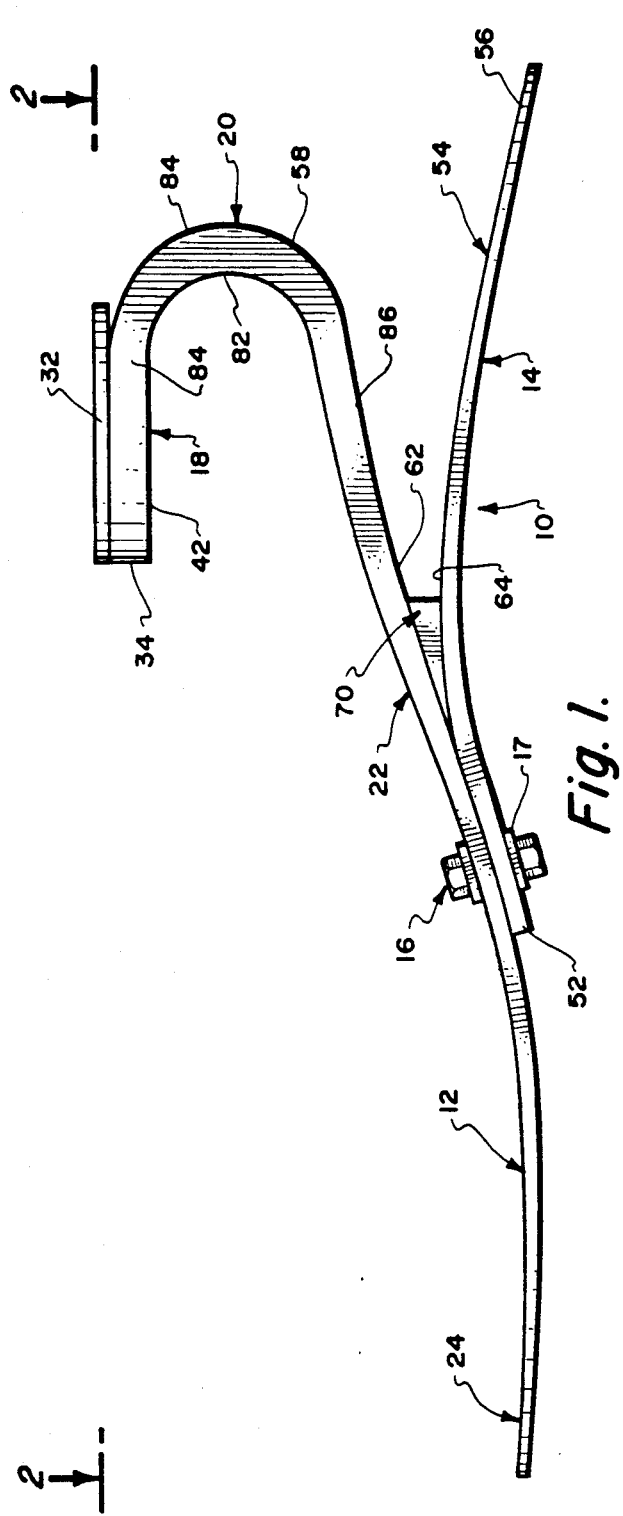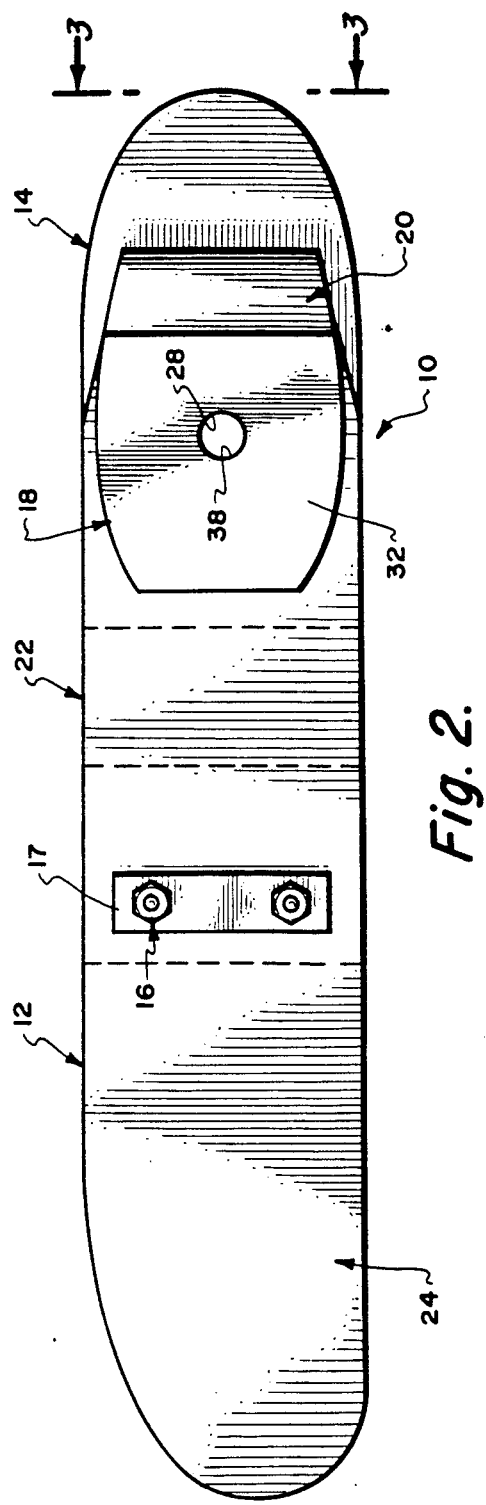

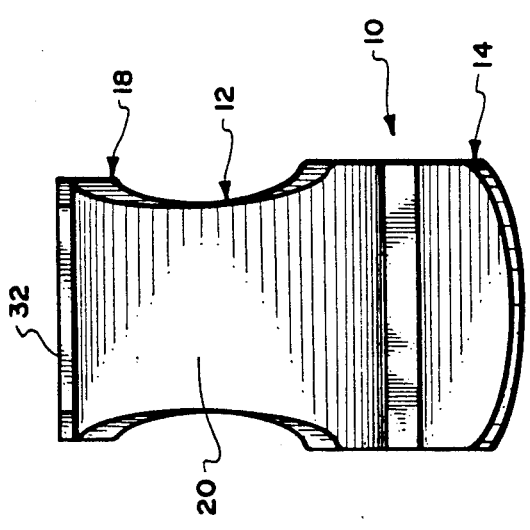
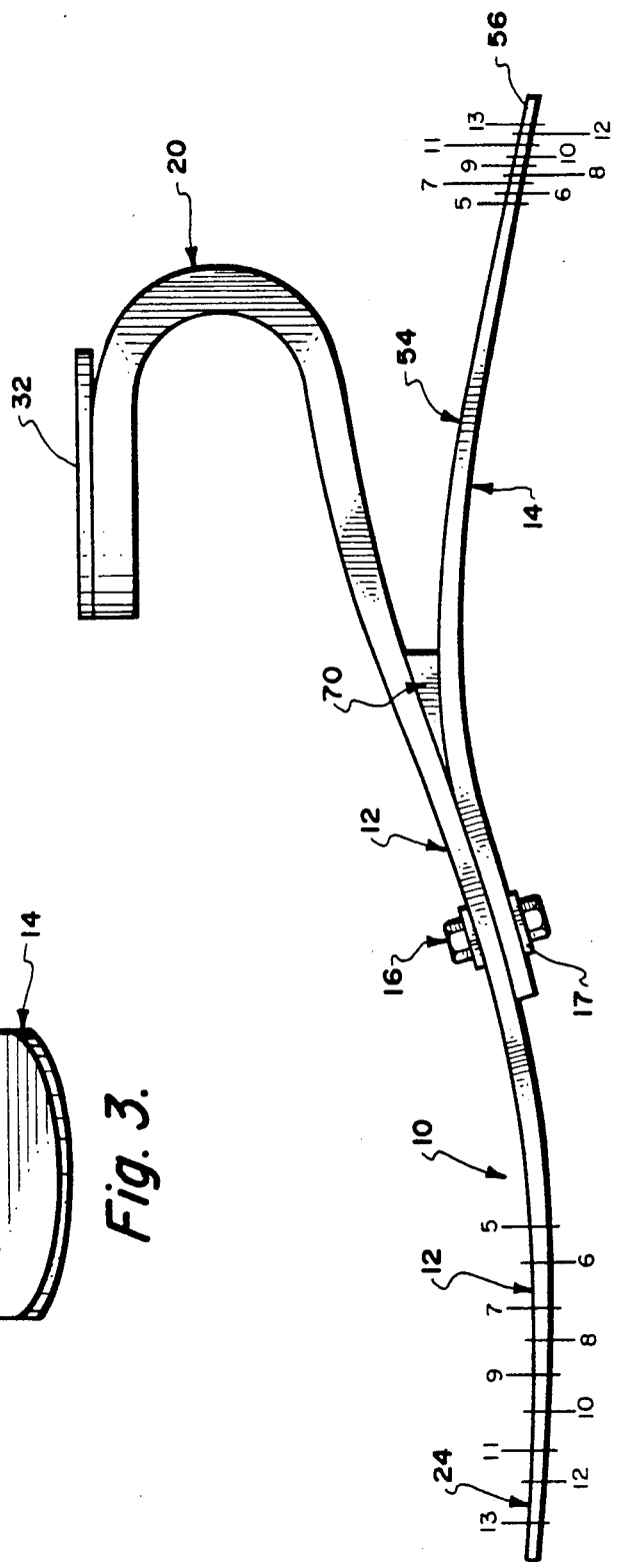

PROSTHETIC FOOT

BACKGROUND OF THE INVENTION

This invention relates to a prosthetic foot and, more particularly to a prosthetic foot which is characterized by the fact that it consists of cooperative forefoot and heel portions which, respectively, incorporate attachment, spring, arch and toe sections and attachment and heel sections.

The prior art relating to prosthetic feet is characterized by a prolixity equal only to the severity of the problem which arises out of the loss of such essential portions of the human body.

The prior art is replete with various types of mechanical devices purporting to solve the foot prosthesis problem. Typical of early devices is Lange 2,075,583, which incorporates a rubber form mounted in operative relationship with a rigid metallic core. Exemplary of the latest developments in the field is Poggi 4,645,509, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

However, none of the prior art devices has been completely succesful because of the fact that the component parts of the prosthesis, as in Lange, are too heavy and too rigid or, as in Poggi, are too massive and monolithic to respond properly to the nuances of stress-response gradients characteristic of the human foot.

One of the primary factors which has inhibited the creation of a successful prosthetic foot has been the fixation of the prior art with the duplication of the structural aspects of the skeletal and muscular components of an actual human foot. In many instances, as exemplified by Poggi '509, mentioned hereinabove, even the toes of the foot are attempted to be duplicated by providing simulacra thereof. It is this fixation upon the mechanical elements of the human foot which has restricted the art to an attempt to duplicate the human foot components, a tendency which is particularly exemplified in Gajdos 3,335,428.

OBJECTS AND ADVANTAGES OF THE INVENTION

The primary object of the invention is the provision of a prosthetic foot which is characterized by a forefoot portion and a heel portion which may be permanently or demountably associated with each other whereby both the forefoot portion and the heel portion can be readily exchanged with correspondingly constructed heel and forefoot portions to provide size adjustment or accommodation of different spring rates to suit the size of foot of the amputee or the stride and weight of the amputee. Therefore, an almost infinite combination of spring rate and size can be provided to the amputee, achieving a natural stride and resilience of gait, which has not been obtainable by prior art prosthetic devices.

Another object of the invention is the provision in a prosthetic foot of the aforementioned character of a forefoot portion which incorporates an attachment section, a curvilinear spring section, an arch section and a toe section. As previously mentioned, the forefoot portion can be provided in different sizes and spring rates, thus permitting the gait weight and size of foot of the amputee to be readily accommodated. Also incorporated in the aforementioned foot is an interchangeable or permanent heel portion which has an attachment section secured to the intersection of the arch and toe sections of the forefoot portion and a heel section extending beyond the curvilinear spring section of the forefoot portion.

Correspondingly, the heel portion can be demountably associated with the forefoot portion of the foot to permit different sizes of heel portion having different spring rates to be mounted in operative relationship with the forefoot portion.

Another object of the invention is the provision of a prosthetic foot of the aforementioned character in which both the forefoot and heel portions of the foot are fabricated from superimposed laminates maintained in operative relationship by an encapsulating polymer, the spring section of the forefoot portion being a cantilever spring and said spring, arch and toe sections of said forefoot portion are susceptible to bending stress determined by the number of the laminates and polymers in the respective spring, arch and toe sections of said forefoot portion.

Similarly, the heel portion is fabricated from superimposed laminates encapsulated in a polymer and capable of spring stress response as heel loads are imposed thereupon during the utilization of said foot.

A further object of the invention is the provision, in a prosthetic foot of the aforementioned character, of a forefoot portion which consists of continuous, integrally and simultaneously formed attachment, curvilinear spring, arch and toe sections, said sections being fabricated as a unitary structure by polymer impregnation of superimposed reinforcing laminae maintained in the desired configuration of said forefoot portion and said spring, arch and toe sections being capable of spring stress generated energy storage whereby the subjection of the toe sections to bending moments will cause uniform transmission of spring stress through said arch and said curvilinear spring sections to said attachment section.

Another object of the invention is the provision of the aforesaid prosthetic foot in which the spring section of said forefoot portion has its upper leg constituted by said attachment section and its lower leg extending into and constituting said arch section, said lacer leg, said arch section and said toe section tapering gradually transversely of the longitudinal axis of said sections to the extremity of said toe section.

A further object of the invention is the provision of the aforesaid prosthetic foot in which an ancillary spring member may be associated with the spring section of said forefoot portion to increase the resistance of said spring section to loads imposed upon the toe section of said foot portion. The concept of the ancillary spring member involves the provision of spring members characterized by different spring rates, which permits the resistance of the spring section to deflection to be precisely adjusted to the weight, activity level and other characteristics of the individual for whom said foot is being adjusted.

The polymers utilized to encapsulate the fibrous laminae are characterized by elasticity and flexibility so that the forefoot and heel portions deflect proportionally to the engagement of said portions with an adjacent surface, causing the resultant energy to be stored and subsequently released when the gait of the amputee incorporating thrust and lift components results in the utilization of the stored energy and a consequent reduction of the energy expended by the amputee. There is a gradual increase in stiffness as the length of the toe section of the forefoot portion shortens due to gradual deflection thereof.

In order to impart a cosmetic aspect to the prosthetic foot, after proper fitting of the foot to insure that the forefoot and heel portions are properly balanced and of appropriate size, the prosthesis may be encapsulated in a suitably shaped foot-like shroud to facilitate the utilization of the prosthetic foot with a conventional shoe. The enclosure must be sufficiently flexible so as not to inhibit the free movement and flexure of the forefoot and heel portions of the prosthetic foot, but, because of the inherently resilient and stress-absorbing characteristics of said foot, little dependence is needed upon the ancillary cushioning action of the enclosure.

Consequently, the foot of my invention is characterized by extreme light weight, instantaneous response to imposed loads and correspondingly instantaneous delivery of stored energy when the gait of the wearer indicates that such stored energy is to be released. Moreover, the foot may be readily mounted in operative relationship with conventional pylons and sockets and can be tuned by the blending of the forefoot and heel portion characteristics to achieve the ultimate in operative response to the needs of the wearer.

Consequently, the wearer of the foot may engage in a wide variety of activities which were precluded in the past because of the structural limitations of prior art prostheses. Running, jumping and other activities are sustained by the foot and it may be utilized in the same manner as the normal foot of the wearer.

Other objects and advantages of the invention will be apparent from the following specification and the accompanying drawings, which are for the purpose of illustration only.

BRIEF DESCRIPTION OF THE DRAWINGS

FIG. 1 is a side elevational view showing the prosthetic foot;

FIG. 2 is a top plan view taken from the broken line 2—2 of FIG. 1;

FIG. 3 is a rear elevational view of the prosthetic foot;

FIG. 4 is a view showing the manner in which different lengths of forefoot and heel portions can be assembled in the desired ideal combination to achieve the maximum stress and flexure combinations of the assembled portions;

DETAILED DESCRIPTION OF PREFERRED EMBODIMENTS

Figure 5:
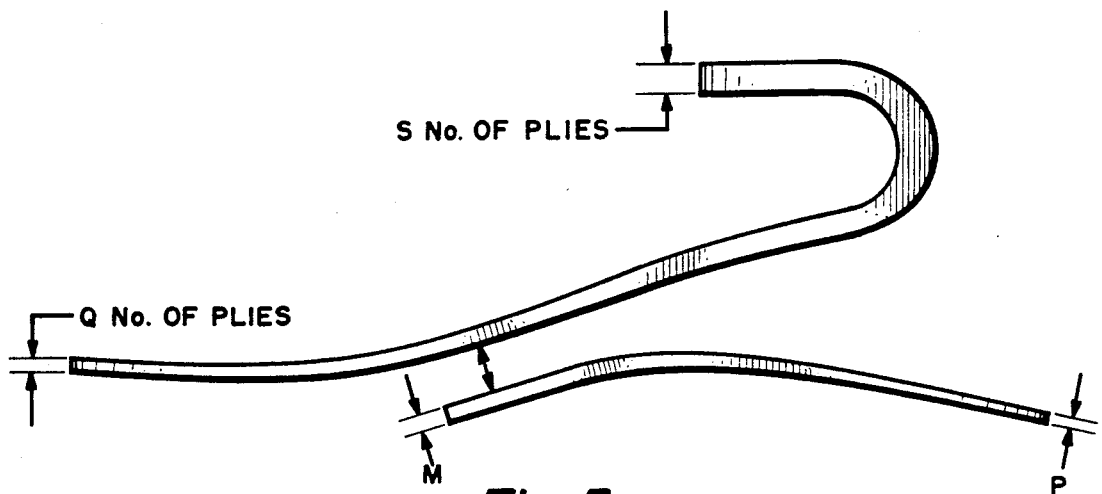
FIG. 5 is a schematic drawing indicating the laminate areas incorporated in the foot and heel portions.

Referring to the drawings, and particularly to FIGS. 1 and 2 thereof, I show a prosthetic foot 10 constructed in accordance with the teachings of the invention and including a forefoot portion 12 and a heel portion 14 operatively and demountably connected to each other by bolt and nut combinations 16 associated with load-transmitting metallic plates 17. If indicated, the forefoot and heel portions can be permanently secured to each other, as by epoxy adhesive or the like.

The forefoot portion 12 of the prosthesis 10 includes a substantially rigid attachment section 18, a curvilinear spring section 20, an arch section 22 and a toe section 24. The forefoot portion 12 of the prosthesis 10 and, more particularly, the sections 18, 20, 22 and 24 are formed integrally with one another and simultaneously by the incorporation of a plurality of laminae embedded in a hardened, flexible polymer.

The attachment section 18 incorporates a centrally-located opening 28 and has a resilient isolation pad 32 secured by a suitable adhesive to the upper surface 34 thereof, for a purpose which will be described in greater detail below. The isolation pad may be formed of synthetic rubber or similar resilient material and incorporates an opening 38 coincident with the opening 28 in the attachment section of the forefoot portion 12 of the prosthesis 10.

The upper surface 34 of the attachment section of the forefoot portion 12 is substantially planar and the under surface 42 thereof is coplanar with the upper surface 34. The attachment section 18 is substantially rigid and is capable of sustaining torsional, impact and other loads impressed thereupon by the forefoot portion 12 and heel portion 14 of the prosthesis 10. In addition, the inherent rigidity of the attachment section prevents it from being distorted in any way and causes the effective transmission of the aforesaid loads imposed thereupon to a suitable ancillary prosthetic pylon, not shown.

As previously mentioned, a cosmetic cover, not shown, can be provided to shroud the prosthesis 10 after the optimum assemblage of the forefoot and heel portions 12 and 14 has been accomplished. Unlike prior art constructions, however, the cosmetic cover, which may be formed of low-density formed polymer, is not required to serve any ancillary shock-absorbing or other stress-isolating function since all of the loads imposed upon the prosthesis can be absorbed, transmitted and reasserted in a manner to be described in greater detail below.

The bolt and nut combinations 16, in conjunction with the load-distributing metallic plates 17, also serve to secure the heel portion 14 in operative relationship with the forefoot portion 12 of the prosthesis 10, as best shown in FIGS. 1-2 of the drawings. The aforesaid mode of affixation facilitates the assembly or dismounting of selected heel portions 14 in operative relationship with selected forefoot portions 12 of the prosthesis 10, thus permitting a wide range of different sizes and stress load response characteristics to be related to each other to accomplish the optimum functional correspondence between the forefoot and heel portions 12 and 14 to accommodate to the maximum extent the needs of the wearer of the prosthesis, and, also, to provide for a proper mating of the prosthesis 10 with a selected, ancillary prosthesis such as a shin pylon or the like.

The heel portion 14, as best shown in FIG. 1 of the drawings, includes an attachment section 52 and a gradually tapering heel section 54 which has its rearward extremity 56 extending beyond the extreme rearward surface 58 of the spring section 20 of the forefoot portion 12 of the prosthesis 10. Mating bores, not shown, in the attachment section 52 of the heel portion 14 and the forefoot portion 12 receive the respective bolt and nut combinations 16 to provide for the aforesaid facility in assembling and disassembling of the forefoot and heel portions 12 and 14.

Interposed between the under surface 62 of the arch section 22 and the upper surface 64 of the heel section 54 is a resilient, spring action function block 70 of wedge-shaped configuration to determine the lever arm of the heel section 54 and isolates the under surface 62 of the arch section 22 and the upper surface 64 of the heel section 54 from each other. The function block 70 may be fabricated from a wide variety of resilient materials, including natural and synthetic rubbers, or the like.

The materials from which the forefoot portion 12 and heel portion 14 are fabricated must be such as to provide an energy-storing, resilient, spring-like effect. This is necessary because each engagement of the prosthesis 10 with an adjacent surface impresses compression, torsional and other loads upon the prosthesis 10 which must be stored within the prosthesis and then, dependent upon the stride of the wearer, be reimpressed upon said surface to achieve a natural stride conforming, ideally, in all respects to the stride of the unimpaired limb of the wearer of the prosthesis 10.

The forefoot and heel portions 12 and 14 of the prosthesis are preferably molded as unitary components and are carefully formed to provide for uniform absorption of stress imposed thereupon. The configuration of both portions 12 and 14 is of utmost importance and the polymer or polymers from which the portions 12 and 14 are fabricated must be resilient and capable of absorbing the compressive, torsional and other stresses referred to hereinabove and of restoring the stored energy created by such stresses, in a natural manner, to the impacted surface which originally imposed such stresses upon the prosthesis 10.

It has been found that there is a limited number of polymers capable of sustaining the significant stresses and repetitive loads imposed upon the prosthesis 10, particularly in the light of the countless numbers of cycles to which the prosthesis 10 is subjected during normal, everyday use.

At present, the best materials for the prosthesis are a composite of high-strength graphite fiber in a high-toughness epoxy thermosetting resin system. There are several reasons for this: (1) the higher strength; (2) stiffness to weight ratio of graphite to other material; (3) The almost complete return of input or stored energy; (4) light weight; (5) high fatigue strength; and (6) minimal creep.

Fiber Glass/Epoxy is a fair choice, but it is not as good as graphite because of lower fatigue strength and higher density. Kevlar is even less acceptable due to poor compression and shear strength, although it is the lowest density of those mentioned.

An important aspect of the polymers referred to hereinabove is that they are characterized by needed, but not excessive, flexural deflection under load, which characteristic permits the shock-absorption stress loading of the prosthesis 10 while maintaining sufficient stability to prevent the collapse of the forefoot and heel portions 12 and 14 of the prosthesis 10 while loads are imposed thereupon.

Because of the reduced thickness of the forefoot and heel portions 12 and 14 of the prosthesis 10, the aforesaid polymers are utilized in conjunction with various laminating materials. Various types of fibrous laminae can be utilized to achieve the continuum required by the design of the forefoot and heel portions 12 and 14 and to complement the stress-absorbing and storing characteristics of the polymers in which said fibrous laminae are embedded.

Of course, there is a wide variety of fibrous reinforcements in the form of laminae available at the present time, including such inorganic fibers as glass or carbon fibers. These inorganic fibers are customarily provided in tape or sheet form and can be readily superimposed in the mold to permit them to be encapsulated in the selected polymer.

Obviously, the number of superimposed laminae and the lengths thereof, together with the thickness of the encapsulating polymer, determine the stress characteristics of the resultant forefoot and heel portions 12 and 14 and, correspondingly, determine the total weight of the prosthesis 10. As will be apparent from the discussion hereinbelow, the individual forefoot and heel portions 12 and 14 are designed to specifically accommodate individuals having different foot sizes, different weights and different strides and the individual design of the forefoot and heel portions 12 and 14 provides for matching, to an extent previously unknown in the art, the natural characteristics of the wearer's uninjured limb.

Furthermore, the function block 70 can be provided in different sizes and in materials having different compression characteristics so that, respectively, the lever arm of the heel section 54 may be increased or decreased and the deflection of the heel section 54 correspondingly increased or decreased.

As previously mentioned, the spring section 20 has a rearward surface 58 and said surface has a forward surface 82 corresponding therewith. It will be noted that the central flexural segment 84 of the spring section 20 is formed integrally with the attachment section 18 and said attachment section constitutes the upper leg of the spring section 20, while the lower leg 86 constitutes the initiation of the arch section 22 of the forefoot portion 12. The configuration of the spring section 20 is the means whereby compressive loads imposed during impingement of the forefoot and heel portions 12 and 14 upon an adjacent surface are absorbed and subsequently reimposed upon said surface. The spring portion 20 is so designed that it functions, substantially, as an ankle joint to permit pivoting of the foot portion 12 thereabout in a manner analogous to the manner in which the normal foot pivots about the normal ankle joint about an axis transversely of said ankle joint.

The lower leg 86 of the spring section 20 provides the gradually tapering arch section 22 which blends into the tapered toe section 24, said taper being achieved by matching parabolic curvatures of the upper and lower surfaces thereof.

The radii of the outer and inner surfaces 58 and 82 of the spring section 20 correspond to provide for the inherent resilience and the major deflection of the forefoot section 12 while inhibiting undesired, excessive collapse of the spring section 20.

It will be noted that the attachment section 52 of the heel portion 14 is substantially rigid and that the deflection of the heel section 54 occurs immediately adjacent the rearward extremity 56 of said heel section, terminating immediately adjacent the function block 70. Obviously, a greater length function block 70 reduces the lever arm of the section 54 of the heel portion 14 and correspondingly reduces the modulus of deflection of said heel section, while a smaller length function block 70 increases the lever arm and correspondingly increases the deflection of the heel section 54 under load.

As best illustrated in FIG. 4 of the drawings, by the numerals appearing at the forward extremity of the toe section 24 of the forefoot portion 12 and the rearward extremity 56 of the heel portion 14, the toe section 24 and heel section 54 can be provided in different lengths to correspond to the size of the foot of the wearer of the prosthesis 10. However, when such different lengths are provided, corresponding reductions in the number of laminae and thickness of taper of the respective toe section 24 and heel section 54 must be made to provide for the proper flexure of said toe and heel sections. It should also be noted that, even with the shortest heel section 54, the rearward extremity 56 thereof projects beyond the rearward surface 58 of the spring section 20 of the forefoot portion 12. Consequently, the stabilizing and stress-absorption characteristics of the heel portion 14 of the prosthesis 10 are always maintained and there is no need for the spring section 20 of the forefoot portion 12 to operate as a heel element of the prosthesis.

By calculation and computation, I have discovered that the requisite number of laminae for different weights of individuals in the forefoot portion 12 and heel portion 14 are as follows:

| Weight Category | M | P | S No. of Plies | Q No. of Plies |
|---|---|---|---|---|
| A | 18 | 27 | 60 | 14 |
| B | 19 | 30 | 62 | 16 |
| C | 21 | 33 | 65 | 17 |
| D | 23 | 33 | 68 | 17 |
| E | 25 | 36 | 70 | 19 |
| F | 28 | 39 | 73 | 21 |
| G | 31 | 42 | 78 | 22 |
| H | 34 | 45 | 83 | 24 |
| I | 37 | 47 | 87 | 27 |

Each ply is 0.0058 inches thick. Plies drop off in a definite manner to achieve desired stiffness and strength of foot.

The relevant areas of the prosthetic foot 10 alluded to in the above-referenced table are shown diagrammatically in FIG. 5 of the drawings. For instance, in weight category C there are 21 plies or laminates incorporated in the attachment section 52 of the heel portion 14 and 33 laminates incorporated in the heel section 54 of the heel portion 14. Similar considerations apply to the designation S for the attachment section 18 of the foot portion and the toe section Q of the same.

It will, of course, be obvious to those skilled in the art that the plies may be fayed or tapered to accomplish a gradual transition as the number of plies is reduced in any area of the foot or heel portions.

Moreover, if a relatively lightweight individual partakes in sports or other activities which subject the prosthesis 10 to greater loads, a heel or forefoot portion 14 and 12 will be fitted which will accommodate for those greater loads.

The spring section 20 is relatively large and forwardly opening, permitting downward deflection toward the heel section 54 and compression of the upper and lower legs 84 and 86 toward each other. Therefore, when subjected to vertical compression loads, it absorbs such loads and distributes them by relative movement of the upper and lower legs 84 and 86 toward each other and toward the heel section 54.

Consequently, there is no stress concentration, either in the impact phase when the adjacent surface is initially contacted by the wearer of the prosthesis 10 or when return of the accumulated forces stored in the prosthesis 10 is accomplished.

The parabolic taper of the toe section 24 continues to the outer extremity thereof and the corresponding curvature of the upper and lower surfaces of the toe section 24 provide for maximum accommodation of said section during surface contact in both the impact and delivery phases of the prosthesis 10. Similar considerations apply to the gradual taper of the heel section 54 of the heel portion of the prosthesis 10. It will be noted that the arcuate, parabolic curvature of the heel section 54 of the heel portion 14 provides for a relatively extended lever arm which achieves stability and, also, stress storage and stress reaction.

The preferred method of manufacturing the forefoot and heel portions 12 and 14 of the prosthesis 10 is by a thermosetting molding process including the utilization of molds having properly shaped and sized cavities. The cavities are designed to receive the requisite number of laminates and the proper volume of polymer.

The design of the foot 10 was based on two major design criteria and several minor criteria. The major ones are: (1) the foot must be structurally adequate (have necessary fatigue in single cycles strength), and (2) it must have proper feel (stiffness/spring and low weight).

The strength is calculated by using the simple straight and curved beam theory. The basic equation for stress due to bending is:

$$\sigma = \frac{KMC}{I}$$

Where:
$\sigma$ = Internal stress.
K = Factor to account for curvature. (K = 1 for straight beam.)
M = Moment = load x moment arm.
C = Distance from neutral axis to point of interest.
I = Moment of inertia of desired cross section.
The basic equation for stress due to shear is:

$$\tau = \frac{VQ}{Ib}$$

T = Shear stress.
Q = Area moment.
V = Shear load.
I = Moment of inertia.
b = Width of part.

The structural analysis is based on a worst-loading condition. This is a vertical point load at the toe tip V, FIG. 6.

The thickness and layup angles of graphite fiber angles vary along the length of the foot. This changes the variables in the equation continuously. Therefore, a computer program was written to calculate the shear and bending stress at several locations along the foot (approximately twenty). The stresses were then compared against allowable stresses to assure that no failure would occur. The thicknesses were adjusted to cause the stresses to be as near to uniform along the length so that no section would fail at a sizably lower load.

Based on empirical data, for the foot to have the desired spring, the deflection at the toe due to a toe load equal to a person's body weight equals three inches for a moderately active person. The basic equation for deflection of a cantilever beam is:

$$Q = \frac{VL^3}{3EI}$$

Figure 6:
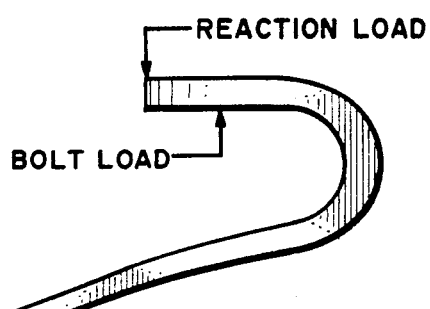
FIG. 6 is a drawing illustrating the dynamic forces to which the foot portion is subjected.

Where, as shown in FIG. 6:
Q=Deflection.
V=Toe load.
l=Length of beam.
E=Modulus or stiffness of material.
I=Moment of inertia of cross section.

This equation is for a constant thickness beam. Since the foot is not a constant thickness, this equation is only good for a small length of foot. A computer program has been written that separated the foot into several small constant thickness beams and added the deflection and rotation for each beam segment to compute the toe deflection. The thicknesses were adjusted to achieve the desired deflection. The equation was modified to make allowances for the curvature of the foot portion, particularly in the spring section thereof.

Unlike prior art unitary devices, the fitting of the prosthesis 10 involves the judicious adjustment of the prosthesis by the proper combination of forefoot and heel portions 12 and 14, respectively. It also involves the selection of the properly designed ancillary leg prosthesis which can be secured by means of the openings 28 and 38 to the attachment section 18 of the forefoot portion 12. Only when the proper correlation between the forefoot portion 12, heel portion 14 and ancillary prosthesis has been accomplished, can the cosmetic shroud, not shown, be installed upon the assembled, respective portions of the prosthesis 10.

Figure 7:
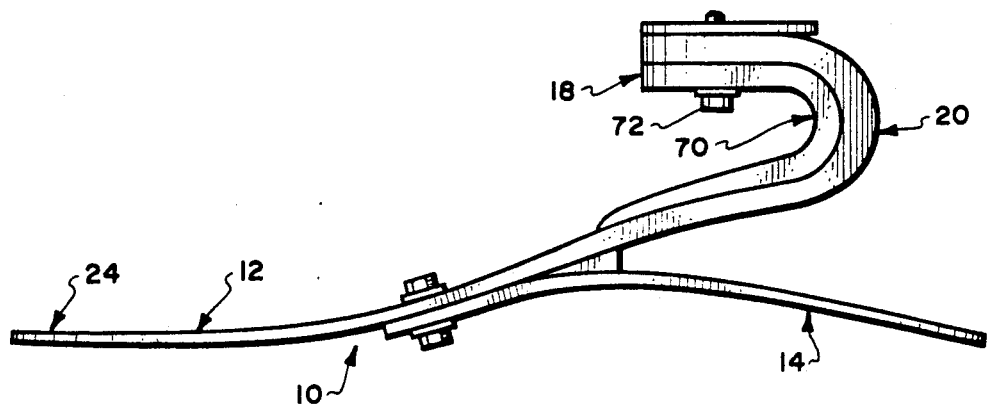
FIG. 7 is a side elevational view illustrating the prosthetic foot equipped with an ancillary spring member.

Of material assistance in fine-tuning the prosthesis 10 is an ancillary, auxiliary spring 70, FIG. 7, which is formed from fibrous laminates of the same character as the various portions of the prosthesis 10. The auxiliary spring 70 is adapted to be secured in operative relationship with the foot portion spring section 20 by a securement bolt 72.

The auxiliary spring 70 can be provided with different numbers of laminates to make it more or less compliant to loads transmitted through the spring section 20. Because the spring section 20 can be provided in a reduced thickness if the spring 70 is used, truer vertical compression of legs 84 and 86 can be achieved.

Consequently, when confronted with various anomalies in an amputee, such as overweight or excess activity levels, the basic structure of the foot portion 12 and, more particularly, the spring section 20 can be materially modified to provide foot portion action which is precisely adjusted to the needs of the amputee.

By the prosthesis of my invention I provide a foot which can be carefully matched to the weight, stride and physical characteristics of the wearer. This is accomplished by carefully balancing the respective physical characteristics of the forefoot portion 12 and the heel portion 14 and the various sections thereof.

Moreover, the assembled prosthesis is far lighter in weight than prior art prostheses since the inherent design and structure of the prosthesis, the materials used and the careful calculation of stress factors of the components of the prosthesis permit fine-tuning of the prosthesis to the needs of the wearer thereof.

I claim:

1. In a prosthetic foot, the combination of: a forefoot portion incorporating an attachment section, a curvilinear spring section, an arch section and a toe section, said arch and toe sections intersecting one another; and a heel portion having an attachment section secured to said intersection of said arch and toe sections and a heel section extending beyond said curvilinear spring section.

2. In a prosthetic foot, the combination of: a forefoot portion incorporating an attachment section, a curvilinear spring section, an arch section and a toe section, said arch and toe sections intersecting one another; and a heel portion having an attachment section secured to said intersection of said arch and toe sections and a heel section extending beyond said curvilinear spring section, in which said attachment section of said forefoot portion has substantially parallel, planar upper and lower surfaces to facilitate the attachment of an ancillary prosthetic device to said forefoot portion of said foot.

3. The prosthetic foot of claim 1 in which said forefoot portion spring section is a cantilever spring and said forefoot is fabricated from superimposed laminates maintained in operative relationship by an encapsulating polymer and said spring, arch and toe sections of said forefoot portion are susceptible to bending stress determined by the thickness of the laminates in the respective spring, arch and toe sections of said forefoot portion.

4. The forefoot of claim 3 in which said heel portion is fabricated from superimposed laminates encapsulated in a polymer and capable of spring stress response as heel loads are imposed thereupon during the utilization of said foot.

5. In a prosthetic foot, the combination of: a forefoot portion incorporating an attachment section, a curvilinear spring section, an arch section and a toe section, said arch and toe sections intersecting one another; and a heel portion having an attachment section secured to said intersection of said arch and toe sections and a heel section extending beyond said curvilinear spring section, in which an auxiliary spring member abuts said curvilinear spring section and is secured in operative relationship therewith.

6. The prosthetic foot of claim 1 or claim 2 or claim 3 or claim 4 or claim 5 in which said heel portion is demountably attached to said forefoot portion to permit heel portions having different spring rates to be secured to said forefoot portion of said foot.

7. In a prosthetic foot, the combination of: a forefoot portion consisting of continuous, integrally and simultaneously formed attachment, curvilinear spring, arch and toe sections, said arch and toe sections being adjacent to one another, said sections being fabricated as unitary structures by polymer impregnation of superimposed reinforcing laminae, said spring, arch and toe sections being capable of spring stress generated energy storage whereby the subjection of said toe section to bending moments will cause uniform transmission of spring stress through said arch and said curvilinear spring sections to said attachment section; and a heel portion secured to said forefoot portion intermediate said toe and arch sections, said heel portion having a rearward extremity extending below and spaced from said curvilinear spring section of said forefoot portion of said foot.

8. In a prosthetic foot, the combination of: a forefoot portion consisting of continuous, integrally and simultaneously formed attachment, curvilinear spring, arch and toe sections, said sections being fabricated as unitary structures by polymer impregnation of superimposed reinforcing laminae, said spring, arch and toe sections being capable of spring stress generated energy storage whereby the subjection of said toe section to bending moments will cause uniform transmission of spring stress through said arch and said curvilinear spring sections to said attachment section; and a heel portion secured to said forefoot portion intermediate said toe and arch portions, said heel portion having its rearward extremity extending beyond said curvilinear spring section of said forefoot portion of said foot, in which said spring section of said forefoot portion has an upper leg constituted by said attachment section and a lower leg extending into and constituting said arch section, said lower leg, said arch section and said toe section tapering gradually in thickness to the extremity of said toe section.

9. In a prosthetic foot, the combination of: a forefoot portion consisting of continuous, integrally and simultaneously formed attachment, curvilinear spring, arch and toe sections, said sections being fabricated as unitary structures by polymer impregnation of superimposed reinforcing laminae, said spring, arch and toe sections being capable of spring stress generated energy storage whereby the subjection of said toe section to bending moments will cause uniform transmission of spring stress through said arch and said curvilinear spring sections to said attachment section; and a heel portion secured to said forefoot portion intermediate said toe and arch portions, said heel portion having its rearward extremity extending below and spaced from said curvilinear spring section of said forefoot portion of said foot, in which a resilient spring member is inserted between the intersecting lower surface of said arch section of said forefoot portion and the upper surface of said heel portion.

10. In a prosthetic foot, the combination of: a forefoot portion consisting of continuous, integrally and simultaneously formed attachment, curvilinear spring, arch and toe sections, said sections being fabricated as unitary structures by polymer impregnation of superimposed reinforcing laminae, said spring, arch and toe sections being capable of spring stress generated energy storage whereby the subjection of said toe section to bending moments will cause uniform transmission of spring stress through said arch and said curvilinear spring sections to said attachment section; and a heel portion secured to said forefoot portion intermediate said toe and arch portions, said heel portion having its rearward extremity extending beyond said curvilinear spring section of said forefoot portion of said foot, in which an auxiliary spring member abuts said curvilinear spring section and is secured in operative relationship therewith.

11. The foot of claim 7 in which said heel portion incorporates an attachment section and a rearwardly tapering heel section which terminates rearwardly of said spring section.

12. The prosthetic foot of claim 7 or claim 8 or claim 11 or claim 9 or claim 10 in which said heel portion is demountably securable to said forefoot portion to facilitate the attachment of said heel portion and the removal thereof to and from said forefoot portion to permit the substitution of heel portions having different spring rates.

13. In a multi-portion prosthetic foot, the combination of: an upper, unitary forefoot portion having a forwardly extending attachment section and a rearwardly extending and forwardly opening spring section, and also having arch and toe sections, all of said sections being formed integrally and simultaneously with one another and being constituted by polymer-impregnated laminates; and a lower heel portion having its forward extremity secured to the underside of said forefoot portion and its rearward extremity extending beyond said spring section of said forefoot portion.

14. The prosthetic foot of claim 13 in which said attachment section is constituted by an upper arm of said spring section and a lower arm of said spring section constitutes the initiation of said arch section of said forefoot portion.

15. The prosthetic foot of claim 13 in which said forefoot portion tapers gradually and uniformly from the lower leg of said spring section to the extremity of said toe section.

16. The prosthetic foot of claim 15 in which said heel portion incorporates an attachment section and a heel section which tapers gradually and uniformly from its intersection with said attachment section to the rearward extremity of said heel section.

17. In a multi-portion prosthetic foot, the combination of: an upper, unitary forefoot portion having a forwardly extending attachment section and a rearwardly extending and forwardly opening spring section, and also having arch and toe sections, all of said sections being formed integrally and simultaneously with one another and being constituted by polymer-impregnated laminates; and a lower heel portion having its forward extremity secured to the underside of said forefoot portion and its rearward extremity extending beyond said spring section of said forefoot portion, in which said heel portion is demountably secured to said forefoot portion to permit the substitution of heel portions having different spring rates in operative relationship with said forefoot portion of said prosthetic foot.

18. In a multi-portion prosthetic foot, the combination of: an upper, unitary forefoot portion having a forwardly extending attachment section and a rearwardly extending and forwardly opening spring section, and also having arch and toe sections, all of said sections being formed integrally and simultaneously with one another and being constituted by polymer-impregnated laminates; and a lower heel portion having its forward extremity secured to the underside of said forefoot portion and its rearward extremity extending beyond said spring section of said forefoot portion, in which an auxiliary spring member abuts said curvilinear spring section and is secured in operative relationship therewith.

19. The prosthetic foot of claim 1 of claim 2 or claim 3 or claim 4 or claim 5 in which a resilient spring member is inserted between the intersecting lower surface of said arch and toe sections of said forefoot portion and the upper surface of said heel portion.

20. The prosthetic foot of claim 14 or claim 15 or claim 16 or claim 18 in which said heel portion is demountably securable to said forefoot portion to facilitate the attachment of said heel portion and the removal thereof to and from said forefoot portion to permit the substitution of heel portions having different spring rates.

21. The prosthetic foot of claim 6 in which a resilient spring member is inserted between the intersecting lower surface of said arch and toe sections of said forefoot portion and the upper surface of said heel portion.

22. The prosthetic foot of claim 7 or claim 8 or claim 11 or claim 9 or claim 10 in which a resilient spring member is inserted between the intersecting lower surface of said arch and toe sections of said forefoot portion and the upper surface of said heel portion.

23. The prosthetic foot of claim 12 in which a resilient spring member is inserted between the intersecting lower surface of said arch and toe sections of said forefoot portion and the upper surface of said heel portion.

* * * * *